United States Patent
Porter et al.

(10) Patent No.: US 9,316,712 B2
(45) Date of Patent: Apr. 19, 2016

(54) MAGNETIC RESONANCE METHOD AND APPARATUS USING DUAL ECHOES FOR DATA ACQUISITION

(75) Inventors: David Andrew Porter, Poxdorf (DE); Christian Schwarzbauer, Cambridge (GB)

(73) Assignees: Siemens PLC, Camberley (GB); Medical Research Council, London (GB)

( * ) Notice: Subject to any disclaimer, the term of this patent is extended or adjusted under 35 U.S.C. 154(b) by 1382 days.

(21) Appl. No.: 12/425,563

(22) Filed: Apr. 17, 2009

(65) Prior Publication Data

US 2010/0268061 A1    Oct. 21, 2010

(51) Int. Cl.
| | |
|---|---|
| G01R 33/565 | (2006.01) |
| A61B 5/055 | (2006.01) |
| G01R 33/48 | (2006.01) |
| G01R 33/561 | (2006.01) |
| A61B 18/00 | (2006.01) |

(52) U.S. Cl.
CPC .......... *G01R 33/56563* (2013.01); *A61B 5/055* (2013.01); *G01R 33/4806* (2013.01); *G01R 33/5618* (2013.01); *A61B 2018/00446* (2013.01)

(58) Field of Classification Search
CPC .......... G01R 33/4806; G01R 33/5615; G01R 33/56563; G01R 33/565
USPC .......... 324/306, 307, 309, 312; 600/345, 410, 600/411
See application file for complete search history.

(56) References Cited

U.S. PATENT DOCUMENTS

| | | | | |
|---|---|---|---|---|
| 5,248,942 A | * | 9/1993 | Ratzel et al. | 324/309 |
| 6,073,041 A | * | 6/2000 | Hu et al. | 600/410 |
| 6,385,479 B1 | * | 5/2002 | Sibbitt | A61B 5/055 324/307 |
| 6,946,839 B2 | * | 9/2005 | Porter | 324/309 |
| 7,417,427 B2 | * | 8/2008 | Porter | 324/306 |
| 2001/0056231 A1 | * | 12/2001 | Jesmanowicz et al. | 600/410 |
| 2002/0057086 A1 | * | 5/2002 | Mueller et al. | 324/307 |
| 2003/0216636 A1 | * | 11/2003 | Paley et al. | 600/410 |

(Continued)

OTHER PUBLICATIONS

Hua-Hsuan Chen, Rex D. Boykin, and Geoffrey D. Clarkea, Routine testing of magnetic field homogeneity on clinical MRI systems, Med. Phys. 33 „11 . . . , Nov. 2006.*

(Continued)

*Primary Examiner* — Amanda Lauritzen Moher
*Assistant Examiner* — Serkan Akar
(74) *Attorney, Agent, or Firm* — Schiff Hardin LLP (57) ABSTRACT

In a method and system for acquiring magnetic resonance image data from a subject, using a data acquisition unit in which a basic magnetic field is generated, a division is designated in a planar section through the subject that divides the planar section into a first section and a second section, with the homogeneity of the basic magnetic field being better in said first section than in said second section. An echo planar imaging sequence is implemented to acquire the magnetic resonance imaging data, with magnetic resonance data being acquired from the first section only from gradient echo signals in the echo planar imaging sequence, and magnetic resonance data from said the second section being acquired from both gradient echo signals and spin echo signals in the echo planar imaging sequence. The method and apparatus are particularly suited for acquiring functional magnetic resonance imaging (fMRI) data from the brain of a subject, in which the first section is an upper portion of the brain and the second section is a lower portion of the brain.

25 Claims, 5 Drawing Sheets

(56) References Cited

U.S. PATENT DOCUMENTS

| | | | |
|---|---|---|---|
| 2004/0044280 A1* | 3/2004 | Paley et al. | 600/410 |
| 2004/0092809 A1* | 5/2004 | DeCharms | 600/410 |
| 2004/0257078 A1* | 12/2004 | Porter | 324/307 |
| 2005/0033154 A1* | 2/2005 | deCharms | 600/410 |
| 2005/0085705 A1* | 4/2005 | Rao et al. | 600/345 |
| 2005/0107682 A1* | 5/2005 | Rao et al. | 600/410 |
| 2005/0197561 A1* | 9/2005 | Elsinger et al. | 600/410 |
| 2005/0237057 A1* | 10/2005 | Porter | 324/307 |
| 2005/0270027 A1* | 12/2005 | Truong et al. | 324/309 |
| 2007/0191704 A1* | 8/2007 | DeCharms | 600/411 |
| 2007/0236217 A1* | 10/2007 | Porter | 324/307 |
| 2007/0252597 A1* | 11/2007 | Posse | 324/312 |
| 2008/0312525 A1* | 12/2008 | Park et al. | 600/410 |

OTHER PUBLICATIONS

Francis et al, "Investigation of cortical dynamics using simultaneous GE and SE EPI", Proc. Intl. Soc. Mag. Reson. Med. 11 (2003).*

"206 TH-PM, Spin-echo EPI—The method of choice for fMRI of brain regions affected by magnetic field inhomogeneities?", Schwarzbauer et al., Human Brain Mapping, Florence, Italy, (2006) p. 206.

"Reduction of Susceptibility Artifact in Gradient-Echo Imaging", Cho et al., Magnetic Resonance in Medicine vol. 23, (1992) pp. 193-200.

"Direct FLASH MR Imaging of Magnetic Field Inhomogeneities by Gradient Compensation", Frahm et al., Magnetic Resonance in Medicine vol. 6, (1988) pp. 474-480.

"Assessment of Relative Brain Iron Concentrations Using $T_2^*$-Weighted and $T_2$-Weighted MRI at 3 Tesla", Ordidge et al., MRM vol. 32, (1994) pp. 335-341.

"Compensation of susceptibility-induced signal loss in echo-planar imaging for functional applications", Cordes et al., Magnetic Resonance Imaging vol. 18, (2000) pp. 1055-1068.

"Optimized EPI for fMRI studies of the orbitofrontal cortex", Deichman et al., NeuroImage vol. 19, (2003) pp. 430-441.

"Compensation of Susceptibility-Induced BOLD Sensitivity Losses in Echo-Planar fMRI Imaging", Deichmann et al., NeuroImage vol. 15, (2002) pp. 120-135.

"Positive or negative blips? The effect of phase encoding scheme on susceptibility-induced signal losses in EPI", De Panfilis et al., NeuroImage vol. 25 (2005) pp. 112-121.

"Optimized EPI for fMRI studies of the orbitofrontal cortex: compensation of susceptibility-induced gradients in the readout direction", Weiskopf et al., Magn. Reson. Mater. Phy. vol. 20, (2007) pp. 39-49.

"Three-dimensional Tailored RF Pulses for the Reduction of Susceptibility Artifacts in $T^*2$-Weighted Functional MRI", Stenger, et al., Magnetic Resonance in Medicine vol. 44, (2000) pp. 525-531.

"3D z-Shim Method for Reduction of Sysceptibility Effects in BOLD fMRI", Gary Glover, Magnetic Resonance in Medicine, vol. 42, (1999) pp. 290-299.

"Composite Image Formation in z-Shimmed Functional MR Imaging", Constable et al., Magnetic Resonance in Medicine, vol. 42, (1999), pp. 110-117.

"Regional Differences of fMR Signal Changes Induced by Hyperventilation: Comparison Between SE-EPI and GE-EPI at 3-T", Naganawa et al., Journal of Magnetic Resonance Imaging, vol. 15, (2002) pp. 23-30.

"Principals of Magnetic Resonance Assessment of Brain Function", David G. Norris, Phd, Journal of Magnetic Resonance Imaging, vol. 23, (2006) pp. 794-807.

"Spin-Echo and Gradient-Echo EPI of Human Brain Activation using BOLD Contrast: a Comparative Study at 1.5 T", Bandettini et al., NMR in Biomedicine, vol. 7, (1994) pp. 12-20.

* cited by examiner

MAGNETIC RESONANCE METHOD AND APPARATUS USING DUAL ECHOES FOR DATA ACQUISITION

BACKGROUND OF THE INVENTION

1. Field of the Invention

The present invention relates to methods and systems for magnetic resonance imaging, and in particular to methods and systems wherein magnetic resonance image data are acquired using an echo planar imaging (EPI) pulse sequence.

2. Description of the Prior Art

Most functional magnetic resonance imaging (fMRI) studies are based on the gradient echo EPI (GE-EPI). In general, this technique is known to be more sensitive to changes in the known BOLD (Blood, Oxygen Level Dependent) contrast than spin echo EPI (SE-EPI). On the other hand, SE-EPI is considerably more robust against signal losses or voids caused by magnetic field inhomogeneities, which typically occur in brain regions near air-tissue interfaces, such as the orbito-frontal cortex or the inferior temporal lobes, as described in Bandettini et al., "Spin-Echo and Gradient-Echo EPI of Human Brain Activation Using Bold Contrast—A Comparative-Study at 1.5 T" NMR in Biomedicine 1994; 7(1-2):12-20 and Norris, "Principles of Magnetic Resonance Assessment of Brain Function," Journal of Magnetic Resonance Imaging 2006; 23(6):794-807. An example is given in FIG. 1 (reproduced from 3. Schwarzbauer et al. "Spin-echo EPI—The Method of Choice For fMRI Of Brain Regions Affected By Magnetic Field Inhomogeneities?," 2006; Human Brain Mapping, Florence, Italy. p 206, which shows an experimental comparison of the BOLD sensitivity obtained by GE-EPI and SE-EPI. In the GE-EPI data, a compete sensitivity loss is observed in large parts of the orbito-frontal cortex, which is reflected by the zero t-score in this region (cf. cross hair). Conversely, the same region exhibits excellent BOLD sensitivity (t-score: 4.6) in the SE-EPI data. This is because the 180° pulse refocuses the phase dispersion caused by static magnetic field inhomogeneities.

Single shot dual echo EPI is an effective method for interleaving the acquisition of GE and SE images: Following the acquisition of a GE EPI image, a slice-selective 180° refocusing pulse is applied and a second (SE EPI) image is acquired such that the spin echo occurs in the centre of k-space of that image. For most fMRI applications, however, this acquisition scheme is suboptimal for a number of reasons.

The main drawbacks of using the single shot dual echo EPI sequence for fMRI are:
(1) More than a 100% increase in the minimum repetition time (TR), because two images are acquired per slice.
(2) The resulting temporal resolution is often insufficient for event-related fMRI designs.
(3) The acquisition scheme is inefficient as signal losses due to magnetic field inhomogeneity typically only occur in the lower third of the brain.
(4) The resulting time normalized SNR is suboptimal (meaning SNR normalized by the square root of the total acquisition time).
(5) The 180° refocusing pulses lead to a substantial increase in the SAR (specific absorption rate). This may be particularly problematic at high and ultrahigh field strength.

SUMMARY OF THE INVENTION

It is an object of the present invention to provide a magnetic resonance imaging method and apparatus that allows images of a region of a subject to be obtained with an improved overall image quality, despite at least a portion of the imaged region being susceptible to inhomogeneities of the basic magnetic field of the magnetic resonance imaging apparatus.

It is a further object of the present invention to provide such a method and apparatus that allows improved brain images to be obtained in fMRI.

These objects are achieved in accordance with the present invention in a method and apparatus wherein, in a planar section through a region of a subject to be imaged, a division is designated that divides the region into two sections, one of which has a better homogeneity than the other. Magnetic resonance image data are obtained from the region using an EPI sequence, with the control protocol for the EPI sequence being modified by the inclusion of the designation of the division, such that magnetic resonance data are acquired from the region exhibiting a better homogeneity using gradient echo signals in the EPI sequence, and magnetic resonance data are acquired only from the region exhibiting the poorer homogeneity using both gradient echo signals and spin echo signals in the EPI sequence.

Thus, the additional SE images are acquired only where necessary, which means for those slices that are actually affected by signal losses or voids in the GE-EPI images.

In an embodiment wherein the region to be imaged is the brain of a subject, the upper region (upper two-thirds) of the brain typically contains fewer voids than the lower region (lower third), and this the designation of the division is made in a sagittal plane section of the brain. The designation can be made manually, such as through an input unit of a computer, which may also be the computer that is used to control the operation of the magnetic resonance data acquisition unit. Alternatively, the designation of the division can be made automatically within the computer, which may again be the actual control unit that operates the magnetic resonance data acquisition system, based on a set of magnetic field maps (possibly calculated from phase maps) acquired before the actual (diagnostic) scan.

DESCRIPTION OF THE PREFERRED EMBODIMENTS

Figure 6:
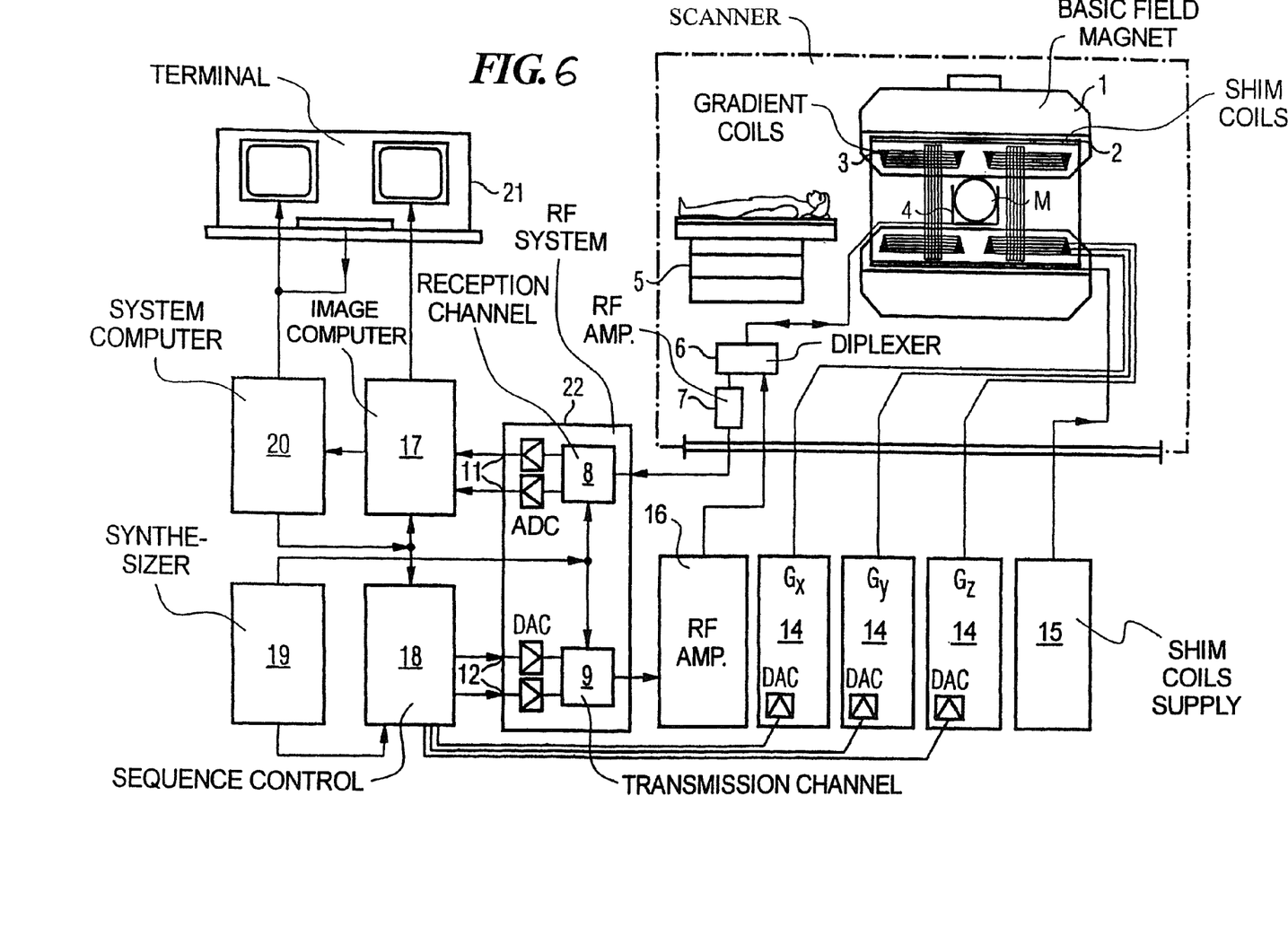
FIG. 6 schematically illustrates a magnetic resonance imaging system constructed and operating in accordance with the present invention.

FIG. 6 is a block diagram schematically illustrating the basic components of a magnetic resonance imaging system that is suitable for implementing the method in accordance with the present invention. The basic structure of the components is known, but either or both of the system computer 20 and the sequence control 18 is/are appropriately programmed with a control protocol for operating the system in accordance with the present invention.

A basic field magnet 1 generates a temporally constant, strong magnetic field for polarization or alignment of the nuclear spins in the examination region of a subject (such as, for example, a portion of a human body to be examined). The high homogeneity of the basic magnetic field that is required for the nuclear magnetic resonance measurement is defined in a spherical measurement volume M into which the portions of the human body to be examined are introduced. Components known as shim plates (not shown) made from ferromagnetic material are applied at suitable points to support the homogeneity requirements and in particular to eliminate temporally invariable influences. Temporally variable influences are eliminated by shim coils 2 that are controlled by a shim power supply 15.

A cylindrical gradient coil system 3 formed by three sub-windings is embodied in the basic field magnet 1. Each sub-winding is provided by an amplifier 14 with current to generate a linear gradient field in the respective direction of the Cartesian coordinate system. The first sub-winding of the gradient field system 3 thereby generates a gradient $G_x$ in the x direction; the second sub-winding generates a gradient $G_y$ in the y direction; and the third sub-winding generates a gradient $G_z$ in the z direction. Each amplifier 14 has a digital/analog converter that is activated by a sequence controller 18 for accurately timed generation of the gradient pulses.

Located within the gradient coils 3 is a radio-frequency antenna 4 that converts the radio-frequency pulses emitted by a radio-frequency power amplifier 16 into an alternating magnetic field to excite the nuclei and align the nuclear spins of the subject to be examined or, respectively, of the region of the subject to be examined. The alternating field emanating from the precessing nuclear spins, i.e. normally the nuclear spin echo signals caused by a pulse sequence made up from one or more radio-frequency pulses and one or more gradient pulses, is converted into a voltage that is supplied via an amplifier 7 to a radio-frequency reception channel 8 of a radio-frequency system 22. The radio-frequency system 22 furthermore has a transmission channel 9 in which the radio-frequency pulses for the excitation of the nuclear magnetic resonance signals are generated. In the sequence controller 18, the respective radio-frequency pulses are represented digitally as a series of complex numbers based on a pulse sequence predetermined by the system controller 20. This number series is supplied as a real part and as an imaginary part via respective inputs 12 to a digital/analog converter in the radio-frequency system 22, and from this to a transmission channel 9. In the transmission channel 9 the pulse sequences are modulated to a radio-frequency carrier signal whose base frequency corresponds to the resonance frequency of the nuclear spins in the measurement volume.

The components within the dot-outline are commonly called a scanner.

The switching from transmission operation to reception operation ensues via a transmission-reception diplexer 6. The radio-frequency antenna 4 radiates the radio-frequency pulses for excitation of the nuclear spins into the measurement volume M and samples resulting echo signals. The correspondingly acquired nuclear magnetic resonance signals are phase-sensitively demodulated in a reception channel 8 of the radio-frequency system 22 and are converted into real part and imaginary part by a respective analog/digital converter. An image is reconstructed by an image computer 17 from the measurement data acquired in this manner. The administration of the measurement data, the image data and the control programs ensues through the system computer 20. The sequence controller 18 monitors the generation of the respective desired pulse sequences and the corresponding scanning of k-space based on a specification with control programs. The sequence controller 18 in particular controls the accurately timed switching of the gradients, the emission of the radio-frequency pulses with defined phase and amplitude and the acquisition of the nuclear magnetic resonance signals. The time base for the radio-frequency system 22 and the sequence controller 18 is provided by a synthesizer 19. The selection of corresponding control programs to generate a magnetic resonance image, as well as the representation of the generated magnetic resonance image; ensue via a terminal 21 that has an interface that includes a keyboard and one or more monitors.

Figure 1:
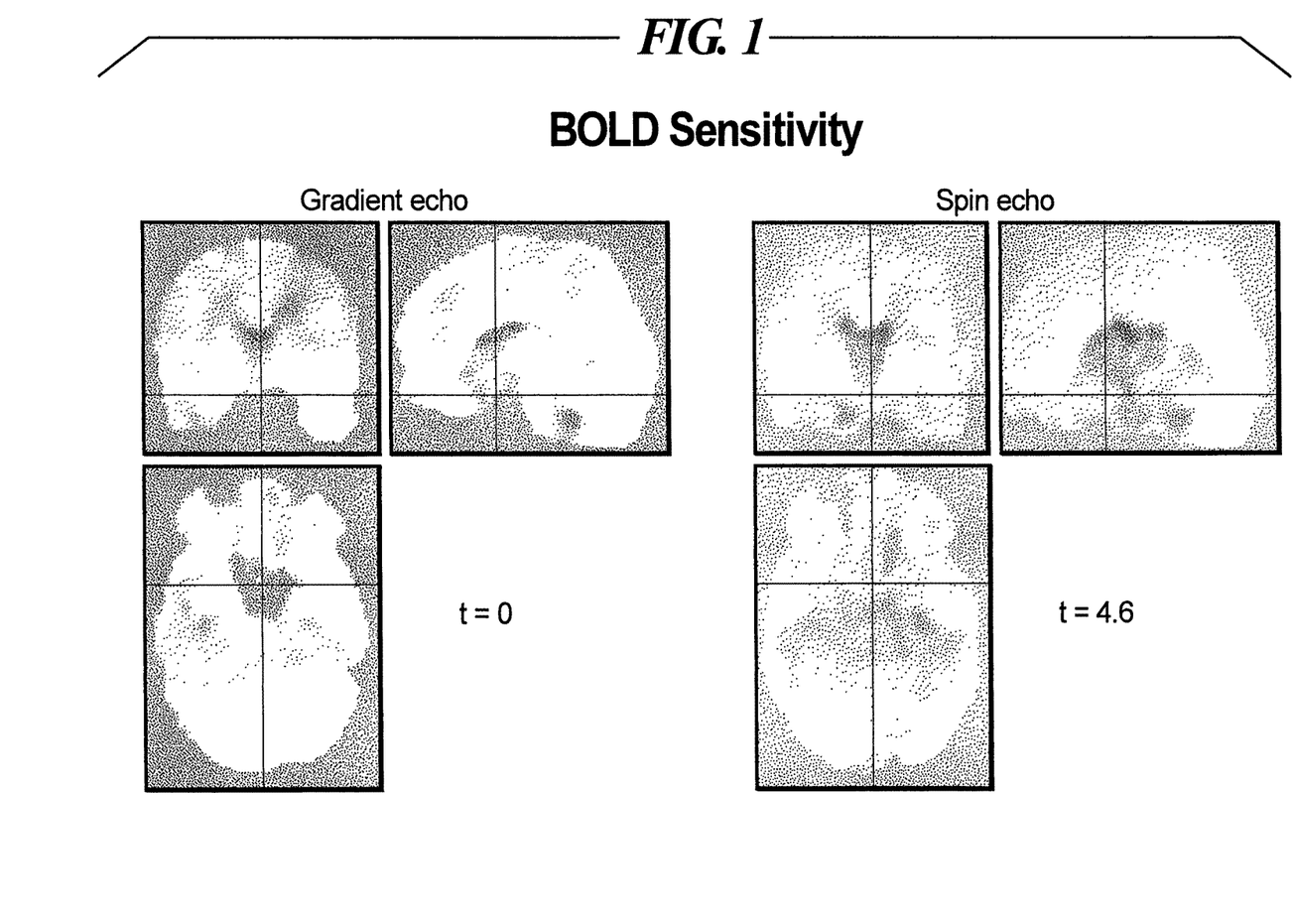
FIG. 1, as noted above, compares BOLD sensitivity for gradient echo EPI and spin echo EPI.
Figure 2:
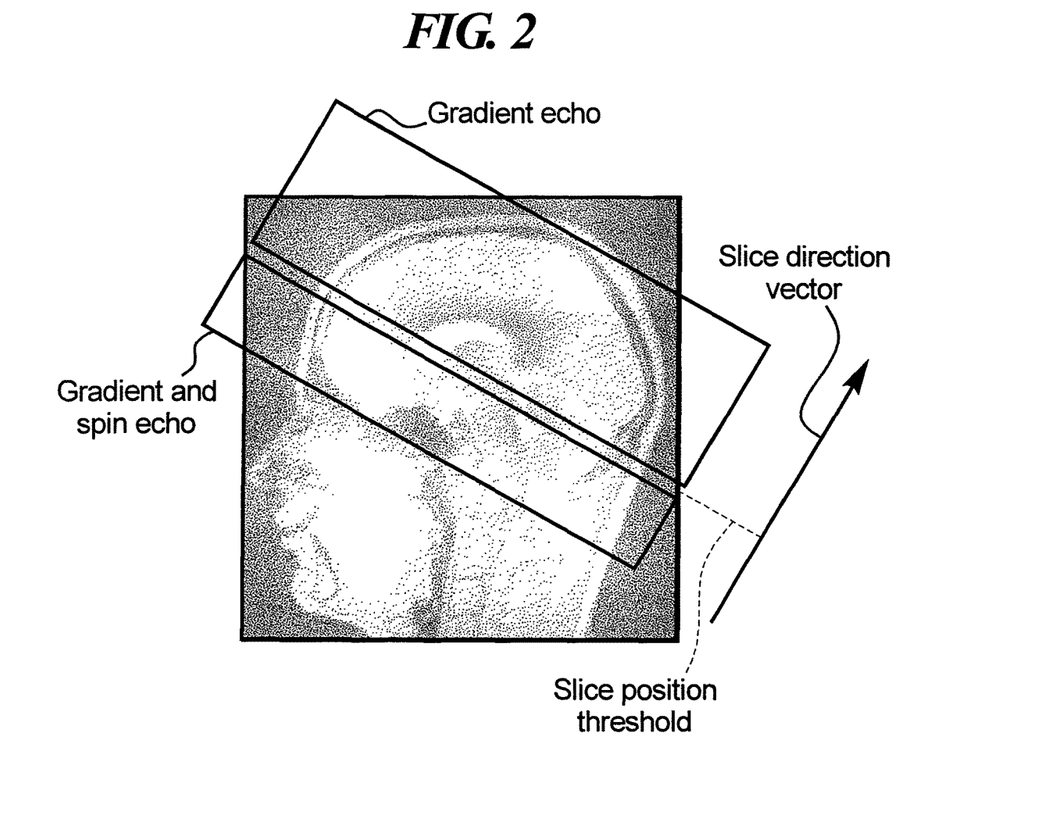
FIG. 2 schematically illustrates the data acquisition scheme in accordance with the present invention, in the context of fMRI.
Figure 3:
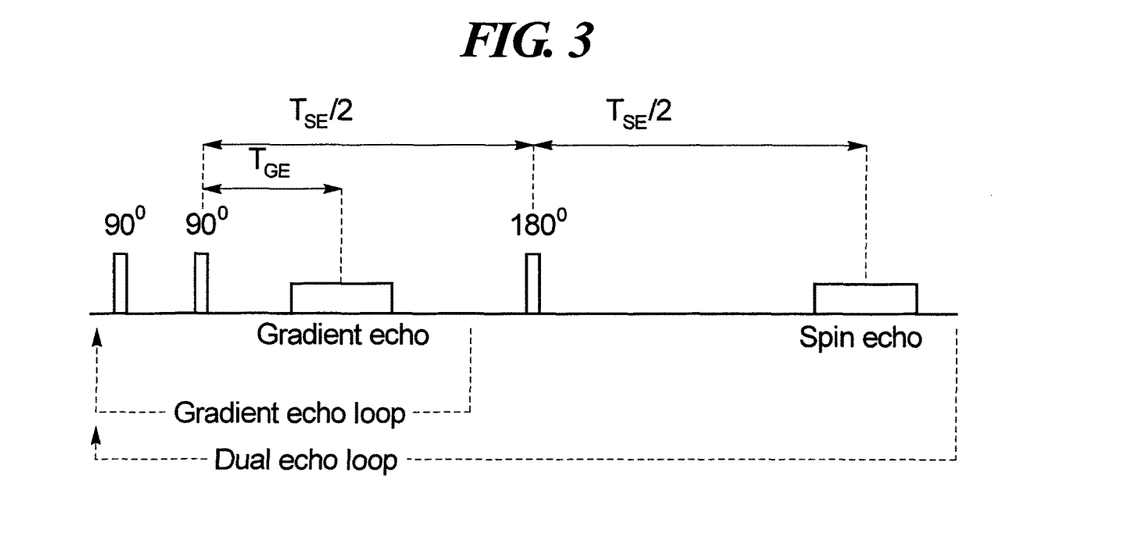
FIG. 3 schematically illustrates an embodiment of a basic pulse sequence in accordance with the present invention, embodying a variable loop structure.

Either the system computer 20 or the sequence control 18 in the apparatus of FIG. 1 is programmed (configured) in accordance with the present invention to implement a data acquisition procedure, as schematically illustrated in FIG. 2, in accordance with the sequence shown in FIG. 3.

The basic concept of the method and system according to the invention is illustrated in FIG. 2. The acquisition scheme disclosed herein is referred to as SPADE (Single shot Partial Dual Echo) imaging. Typically, magnetic field inhomogeneities only affect the lower third of the brain. By restricting the acquisition of additional SE images to this region, SPADE provides a much more efficient acquisition scheme than the conventional single shot dual echo approach. This not only considerably reduces the minimum TR, but also enables whole brain coverage in less than 2.9 s (32 slices, slice thickness: 3 mm, matrix size: 64×64), providing a temporal resolution sufficient for most event-related fMRI designs. The time normalized SNR can be considered optimal, as no time is wasted with acquiring SE-images that are not actually needed. The reduced number of spin echoes also results is a significantly lower SAR, which makes SPADE particularly attractive for high and ultrahigh field applications. Furthermore, SPADE can be easily combined with parallel imaging acquisition schemes, which is particularly useful for fMRI studies where high spatial resolution is required.

The SPADE sequence was implemented on the Siemens Tim TRIO system at the MRC Cognition and Brian Sciences Unit in Cambridge. The sequence diagram is shown in FIG. 3. The sequence code is based on the Siemens product EPI sequence (epifid), which was adapted to accommodate additional spin echoes. This also involved a modification of the corresponding ICE code. The implementation is fully compatible with iPAT.

Two new imaging parameters were included on the Sequence/Special card: 'Slice position threshold' (editable) and 'Number of spin echoes' (non-editable). Additional spin-echoes are only acquired for the slices below the slice position threshold and the corresponding number of spin echo images is calculated and displayed. If the slice position threshold is set to a value greater than the most positive slice position, spin echo images will be acquired for all slices, similar to the conventional single shot dual echo sequence.

The SPADE sequence shown in FIG. 3 is basically a single shot dual echo EPI sequence with a variable loop structure. The dual echo loop is executed only for slices below a designated slice position, as indicated in FIG. 2, and both gradient and spin echo images are acquired for these slices. For all other slices, only the gradient echo loop is executed, resulting in a single gradient echo image per slice.

Figure 4:
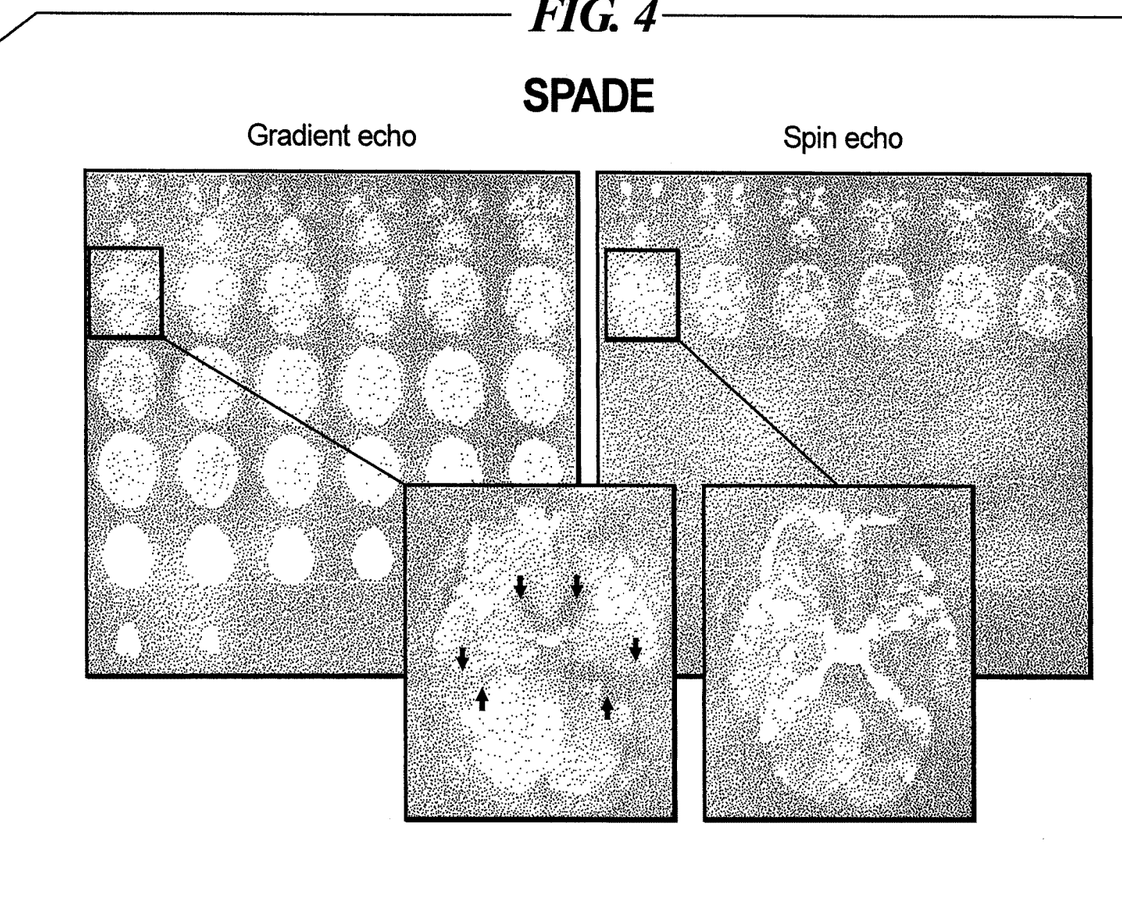
FIG. 4 shows results obtained in a healthy volunteer using the sequence in accordance with the present invention.

FIG. 4 shows the results obtained in a healthy volunteer. 32 transversal-oblique slices were acquired to cover the whole brain (slice thickness: 3 mm, slice gap: 0.75 mm, matrix size:

64×64, field of view: 192×192 mm, in-plane resolution: 3×3 mm). Additional spin echo images were acquired only for the lower 12 slices. The resulting minimum repetition time was TR=2.9 s. The corresponding echo times were 30 and 102 ms. A comparison of the two enlarged images clearly shows that the typical signal voids visible in the gradient echo image (indicated by arrows) are absent in the spin echo image.

Figure 5:
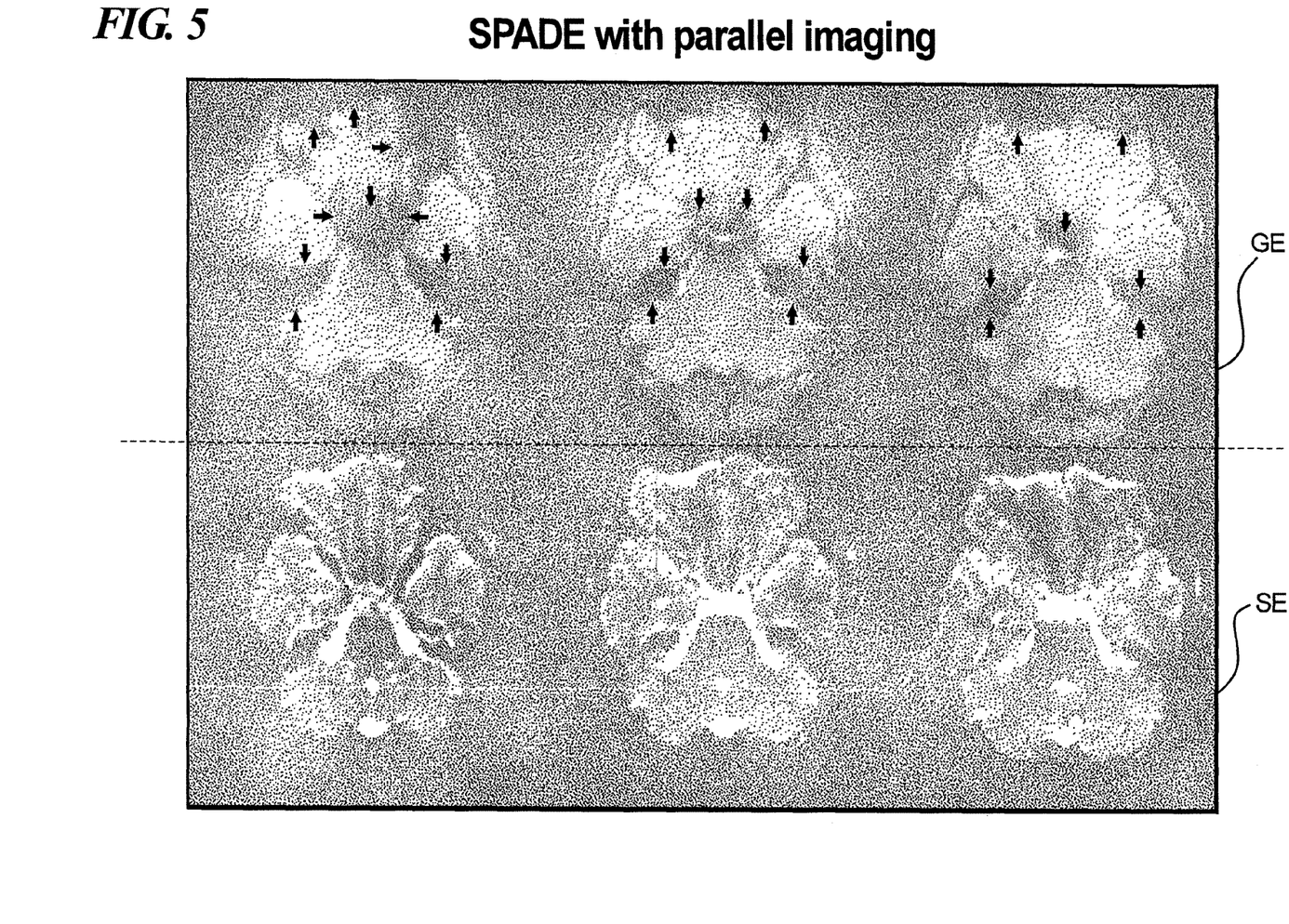
FIG. 5 illustrates an example of high-resolution images obtained in accordance with the present invention, using parallel imaging.

In order to demonstrate the parallel imaging capability of SPADE, a high-resolution imaging protocol was set up using the known GRAPPA sequence (acceleration factor: 2, reference lines: 24). The in-plane resolution was 1.8×1.8 mm (matrix size: 106×106, field of view 192×192 mm). 32 transversal-oblique slices (slice thickness: 2.5 mm, slice gap: 1.25 mm) were acquired in a different healthy volunteer. Additional spin echo images were acquired for the lower 12 slices resulting in TR=3.2 s. The echo times were 30 and 107 ms. The gradient and spin echo images of three representative adjacent slices are shown in FIG. 5. Like in the example before, the characteristic signal voids visible in the gradient echo images do not occur in the spin echo images.

SPADE imaging provides a highly effective solution for whole brain fMRI applications. A significant improvement of the BOLD sensitivity can be achieved in areas of magnetic field inhomogeneity (e.g. the orbito-frontal cortex or the inferior temporal lobes) at the expense of a comparatively small increase in the TR and SAR. This makes SPADE appropriate for fMRI applications where whole brain coverage (and sensitivity) is required. Moreover, SPADE can be easily integrated with the commercially available Siemens EPI product sequence including features such as partial k-space sampling and parallel imaging.

In the embodiment of SPADE described herein, the slice position threshold (cf. FIG. 2) has to be specified by the user. However, this requires some specific knowledge about the nature of the signal losses in GE-EPI. It is thus possible to implement a procedure that does not involve any user interaction at all, wherein a suitable value for the slice position threshold is simply derived from a set of magnetic field maps is acquired before the actual (diagnostic) fMRI scan. The complete processing chain would therefore include the following steps: acquisition of field maps (or more precisely the phase maps from which the field maps can be calculated), calculation of the slice position threshold, forwarding of this value to the SPADE sequence, and fMRI data acquisition using the optimized SPADE sequence.

The entire procedure can be fully automated within the framework of the current IDEA programming environment.

A number of alternative methods have been proposed for reducing signal losses caused by magnetic field inhomogeneities. The most common approach is the z-shimming method, as described in Frahm et al., Direct FLASH MR Imaging of Magnetic-Field Inhomogeneities by Gradient Compensation" Magnetic Resonance in Medicine 1988; 6(4):474-480, which combines multiple images of the same slice, each acquired with a different compensation gradient pulse applied along the slice direction. The z-shimming method has been extended by applying an additional compensation gradient in phase encode direction (Deichmann et al. "Compensation of Susceptibility-Induced BOLD Sensitivity Losses in Echo-Planar fMRI Imaging," Neuroimage 2002; 15(1):120-135) and it has been shown that the polarity of the phase encoding gradient plays an important role (De Panfilis et al. "Positive or negative blips? The effect of phase encoding scheme on susceptibility-induced signal losses in EPI," Neuroimage 2005; 25(1):112-121). The acquisition of multiple images per slice compromises the temporal resolution in fMRI.

The partial acquisition scheme used in SPADE could be adapted and combined with z-shimming, in which case two or more images per slice would only be acquired where necessary, i.e. for slices affected by signal losses or voids. Because typically only the lower third of the brain is affected, this would result in a considerable improvement of the temporal resolution. The partial acquisition scheme could be implemented either as a single-shot or a multi-shot sequence. In the single-shot approach, the acquisition of the GE-EPI image would be followed by one or more asymmetric SE-EPI images, each preceded by a different z-shim gradient. The asymmetric spin echo ensures that the sensitivity to T2* changes is maintained. In the multi-shot approach, a complete volume of GE-EPI images would be acquired before acquiring one or more partial volumes with different z-shim gradients. As possible difficulty may arise, however, from the T1 related signal changes caused by the shorter repetition time of the partial volume acquisition.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for acquiring magnetic resonance image data, comprising the steps of:
   providing a magnetic resonance scanner operated by a control computer and having a magnet system that generates a basic magnetic field;
   using said control computer, making a designation of a division to place a dividing line in a planar section through a human or animal subject, dependent on anatomy represented in said planar section, that selectively divides said planar section into, and establishes in said planar section, a division comprising a first selected section on one side of said dividing line in which said basic magnetic field has a first homogeneity and a second selected section, on an opposite side of said dividing line and separated from said first selected section by said dividing line, in which said basic magnetic field has a second homogeneity that is less homogenous than said first homogeneity;
   after making said division, using said control computer to generate a control protocol incorporating the designation of said division, that operates said magnetic resonance scanner to acquire magnetic resonance image data from the subject using an echo planar imaging sequence in which, according to said designation of said division, magnetic resonance image data are acquired from said first selected section only from gradient echo signals in said echo planar imaging sequence and magnetic resonance image data are acquired from said second selected section from both gradient echo signals and spin echo signals in said echo planar imaging sequence;
   operating said magnetic resonance scanner from said control computer according to said control protocol to acquire said magnetic resonance image data from the subject; and
   making the magnetic resonance image data from the subject available as an output from the control computer in a form allowing reconstruction of a visible image of the subject therefrom.

2. A method as claimed in claim 1 comprising using an image computer to reconstruct said visible image of the subject from said magnetic resonance image data that are output from the control computer.

3. A method as claimed in claim 1 comprising designating said division in said planar section by placing said dividing line at a location of a predetermined homogeneity threshold in said planar section.

4. A method as claimed in claim 1 comprising acquiring said magnetic resonance data from the brain of the subject, and designating said division in a sagittal section, as said planar section, through the brain of the subject.

5. A method as claimed in claim 4 comprising designating said division to divide the brain of the subject in said sagittal section into an upper region, closer to a top of the head of the subject, as said first selected section, and a lower region, farther from the top of the head of the subject, as said second selected section.

6. A method as claimed in claim 5 comprising designating said division with said upper region encompassing two-thirds of the brain of the subject in said sagittal section and with said lower section encompassing approximately one-third of the brain of the subject in said sagittal section.

7. A method as claimed in claim 1 comprising operating said magnetic resonance scanner according to said control protocol to acquire said magnetic resonance data from successive slices of the subject.

8. A method as claimed in claim 7 comprising generating an echo planar imaging sequence in said control protocol that comprises a 90° focusing pulse, followed by a gradient echo readout gradient in which said gradient echo signal is read out, followed by a 180° refocusing pulse, followed by a spin echo readout gradient in which said spin echo signal is read out, and comprising operating said magnetic resonance scanner according to said control protocol to execute a gradient echo loop comprising said 90° focusing pulse and said gradient echo readout gradient to acquire said magnetic resonance data from successive slices in said first selected section and to execute a dual echo loop, comprising said 90° focusing pulse, said gradient echo readout gradient, said 180° refocusing pulse, and said spin echo readout gradient, to acquire said magnetic resonance data from successive slices in said second selected section.

9. A method as claimed in claim 1 comprising designating said division manually by displaying said planar section and manually placing said dividing line in the displayed planar section via an interface of said control computer.

10. A method as claimed in claim 1 comprising designating said division non-manually, automatically in said control computer by placing said dividing line in said planar section based on a magnetic field map in said planar section of said subject.

11. A method as claimed in claim 1 comprising generating said control protocol as an fMRI protocol and operating said magnetic resonance scanner to acquire said magnetic resonance image data as fMRI data.

12. A method as claimed in claim 1 comprising operating said magnetic resonance scanner to acquire said magnetic resonance data from a plurality of slices of said human or animal subject using said echo planar imaging sequence, by acquiring said magnetic resonance data from said first selected section in a plurality of slices in said first section, and acquiring said magnetic resonance imaging data from said second selected section in a plurality of other slices in said second section.

13. A method as claimed in claim 1 comprising operating said magnetic resonance scanner to acquire said magnetic resonance data from a plurality of slices of said human or animal subject using said echo planar imaging sequence, and acquiring said magnetic resonance data from said first selected section in a plurality of slices in said first section, and acquiring said magnetic resonance imaging data from said second section in a plurality of other slices in said second selected section.

14. A system for acquiring magnetic resonance image data, comprising:
a magnetic resonance scanner having a magnet system that generates a basic magnetic field;
a control computer configured to place a dividing line in a planar section through a human or animal subject, dependent on anatomy represented in said planar section, that selectively divides said planar section into, and establishes in said planar section, a division comprising a first selected section on one side of said dividing line in which said basic magnetic field has a first homogeneity and a second selected section, on an opposite side of said dividing line and separated from said first selected section by said dividing line, in which said basic magnetic field has a second homogeneity that is less homogenous than said first homogeneity;
a control computer configured to generate after making said division, a control protocol that incorporates the designation of said division, and to operate said magnetic resonance scanner to acquire magnetic resonance image data from the subject using an echo planar imaging sequence by, according to said designation of said division, acquiring magnetic resonance image data from said first selected section only from gradient echo signals in said echo planar imaging sequence and acquiring magnetic resonance image data from said second selected section from both gradient echo signals and spin echo signals in said echo planar imaging sequence; and
said control computer being configured to make the magnetic resonance image data from the subject available as an output from the control computer in a form allowing reconstruction of a visible image of the subject therefrom.

15. A system as claimed in claim 14 comprising an image reconstruction computer configured to reconstruct said visible image of the subject from said magnetic resonance data that are output from the control computer.

16. A system as claimed in claim 14 wherein said control computer is configured to designate said division in said planar section by placing said dividing line at a location of a predetermined homogeneity threshold in said planar section.

17. A system as claimed in claim 14 wherein said magnetic resonance data acquisition unit is configured to acquire said magnetic resonance data from the brain of the subject, and wherein said control computer is configured to designate said division in a sagittal section, as said planar section, through the brain of the subject.

18. A system as claimed in claim 17 wherein said control computer is configured to designate said division to divide the brain of the subject in said sagittal section into an upper selected region, closer to a top of the head of the subject, as said first selected section, and a lower selected region, farther from the top of the head of the subject, as said second selected section.

19. A system as claimed in claim 18 wherein said control computer is configured to designate said division with said upper selected region encompassing two-thirds of the brain of the subject in said sagittal section and with said lower selected region encompassing approximately one-third of the brain of the subject in said sagittal section.

20. A system as claimed in claim 14 wherein said control computer is configured to operate said magnetic resonance scanner according to said control protocol to acquire said magnetic resonance data from successive slices of the subject.

21. A system as claimed in claim 20 wherein said control computer is configured to generate an echo planar imaging sequence in said control protocol that comprises a 90° focusing pulse, followed by a gradient echo readout gradient in which said gradient echo signal is read out, followed by a 180° refocusing pulse, followed by a spin echo readout gradient in which said spin echo signal is read out, and to operate said magnetic resonance scanner according to said control protocol to execute a gradient echo loop comprising said 90° focusing pulse and said gradient echo readout gradient to acquire said magnetic resonance data from said first selected section and to execute a dual echo loop, comprising said 90° focusing pulse, said gradient echo readout gradient, said 180° refocusing pulse, and said spin echo readout gradient, to acquire said magnetic resonance data from said second selected section.

22. A system as claimed in claim 14 wherein said control computer comprises an interface that allows manual designation of said division via said interface.

23. A system as claimed in claim 14 wherein said control computer is configured to execute an algorithm to automatically designate said division that places said dividing line in said planar section based on a magnetic field map in said planar section of said subject.

24. A system as claimed in claim 14 wherein said control computer is configured to generate said control protocol for functional magnetic resonance imaging of the brain of the human or animal subject, and to designate said division in a planar section through said brain dependent on voids in said brain that produce said first homogeneity of said basic magnetic field in said first selected section and said second homogeneity of said basic magnetic field in said second selected section.

25. A system as claimed in claim 14 wherein said control computer is configured to operate said magnetic resonance scanner to acquire magnetic resonance data from a plurality of slices in said human or animal subject using said echo planar imaging sequence, and to acquire said magnetic resonance data from said first selected section in a plurality of slices in said first section, and to acquire said magnetic resonance image data from said second selected section in a plurality of other slices in said second section.

* * * * *